United States Patent
Schneider

(10) Patent No.: US 7,788,060 B2
(45) Date of Patent: *Aug. 31, 2010

(54) SYSTEM AND METHOD FOR MEASURING POSITION AND ORIENTATION USING DISTORTION-COMPENSATED MAGNETIC FIELDS

(75) Inventor: Mark R. Schneider, Williston, VT (US)

(73) Assignee: Ascension Technology Corp., Milton, VT (US)

(*) Notice: Subject to any disclaimer, the term of this patent is extended or adjusted under 35 U.S.C. 154(b) by 89 days.

This patent is subject to a terminal disclaimer.

(21) Appl. No.: 12/037,249

(22) Filed: Feb. 26, 2008

(65) Prior Publication Data

US 2008/0162074 A1 Jul. 3, 2008

Related U.S. Application Data

(62) Division of application No. 10/945,277, filed on Sep. 20, 2004, now Pat. No. 7,373,271.

(51) Int. Cl.
*G01B 7/004* (2006.01)
(52) U.S. Cl. .................................... 702/150
(58) Field of Classification Search ................. 702/150
See application file for complete search history.

(56) References Cited

U.S. PATENT DOCUMENTS

| | | |
|---|---|---|
| 3,868,565 A | 2/1975 | Kuipers |
| 4,054,881 A | 10/1977 | Raab |
| 4,622,644 A | 11/1986 | Hansen |
| 4,710,708 A | 12/1987 | Rorden |
| 4,737,794 A | 4/1988 | Jones |
| 4,829,250 A | 5/1989 | Rotier |
| 4,945,305 A | 7/1990 | Blood |
| 5,347,289 A | 9/1994 | Elhardt |
| 5,377,678 A | 1/1995 | Dumoulin |
| 5,453,686 A | 9/1995 | Anderson |
| 5,592,939 A | 1/1997 | Martinelli |
| 5,600,330 A | 2/1997 | Blood |
| 6,147,480 A | 11/2000 | Osadchy |
| 6,172,499 B1 | 1/2001 | Ashe |
| 6,427,079 B1 | 7/2002 | Schneider et al. |
| 6,528,989 B1 | 3/2003 | Hansen |
| 2003/0161487 A1* | 8/2003 | Husted et al. .............. 381/94.5 |

FOREIGN PATENT DOCUMENTS

| | | |
|---|---|---|
| WO | WO9404938 | 3/1994 |
| WO | WO9605768 | 2/1996 |

* cited by examiner

*Primary Examiner*—Tung S Lau
(74) *Attorney, Agent, or Firm*—Downs Rachlin Martin PLLC

(57) ABSTRACT

An electromagnetic tracking system and a distortion compensation method that utilize a lead-lag network model to compensate for position and orientation distortion caused by eddy currents formed in one more conductive distorters located within a tracking environment during electromagnetic tracking of one or more objects. The method is adaptive relative to the amount of distortion cause by the conductive distorters.

5 Claims, 6 Drawing Sheets

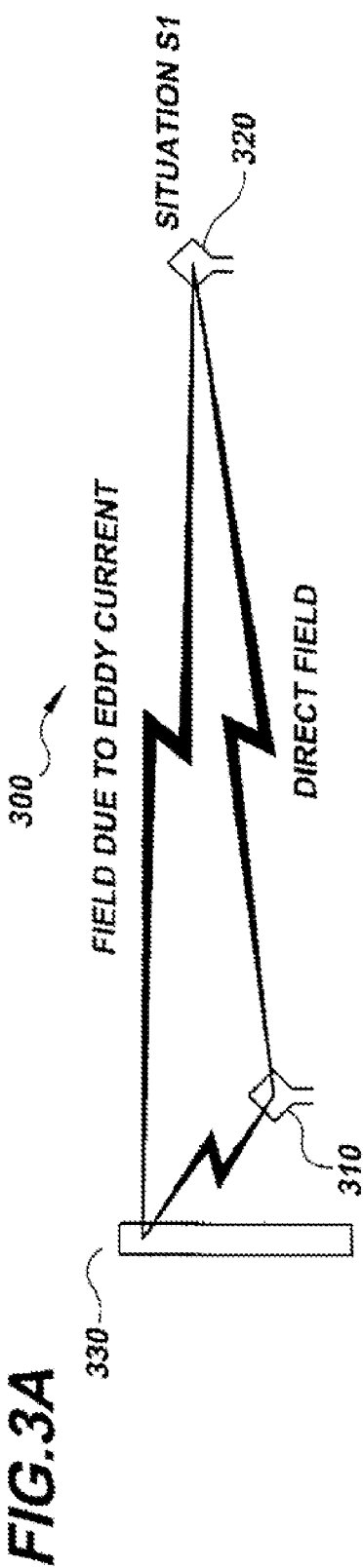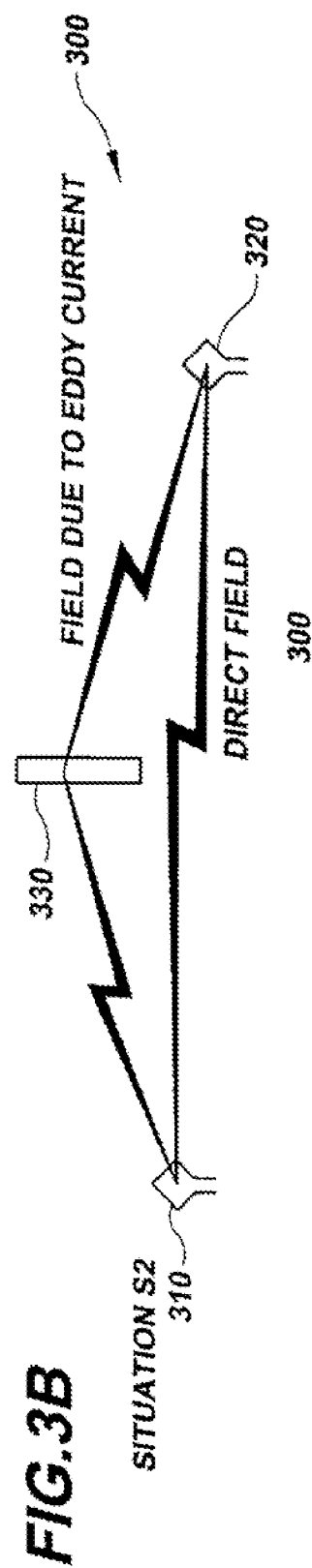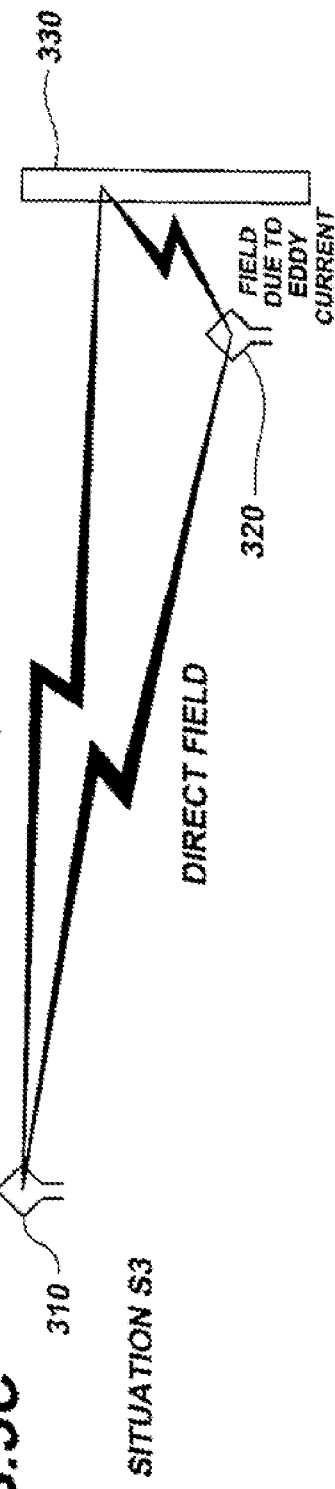

SYSTEM AND METHOD FOR MEASURING POSITION AND ORIENTATION USING DISTORTION-COMPENSATED MAGNETIC FIELDS

CROSS-REFERENCE TO RELATED APPLICATION

This application is a divisional of co-pending U.S. application Ser. No. 10/945,277 filed on Sep. 20, 2004, and incorporated by reference herein.

FIELD OF THE INVENTION

The present invention generally relates to the field of position and orientation sensing. In particular, the present invention is directed to a system and method for measuring position and orientation using distortion-compensated magnetic fields.

BACKGROUND OF THE INVENTION

Determining location parameters, e.g., position and orientation, of objects in free space has many applications, including catheter tracking, digitizing objects and virtual reality, among others. One method that has become successful in these applications relies on the electromagnetic coupling between a source of magnetic fields and one or more sensors of such fields. Variations include AC and pulsed-DC magnetic field generation and single and multiple axes sensors and field generators. Examples of AC systems utilizing a plurality of field generators and sensors are disclosed by Kuipers in U.S. Pat. No. 3,868,565, Raab in U.S. Pat. No. 4,054,881 and Jones in U.S. Pat. No. 4,737,794, among others.

Conventional systems are generally hindered by inaccuracies resulting from the presence of conductive materials, i.e., electrically-conductive, non-ferromagnetic materials such as aluminum and steel, within the tracking environment. These inaccuracies are caused by the flow of eddy currents within these materials. Eddy currents are caused by the time variation of magnetic fields, such as the magnetic fields produced by the field generators. Each time-varying magnetic field induces a corresponding electric field that, in turn, causes an electric current (eddy current) to flow in the conductive material. These eddy currents, in turn, generate their own (secondary) magnetic fields that can interfere with the sensing of the magnetic fields of the field generators. These secondary magnetic fields can cause inaccuracies in location parameters.

Conventional magnetic field tracking techniques generally ignore the inaccuracies due to secondary magnetic fields caused by eddy currents. However, it would be desirable to eliminate or minimize these inaccuracies, particularly for applications requiring high accuracies and wherein it is difficult, impractical or undesirable to remove conductive materials from the tracking environment. Examples of such applications include the tracking of medical devices within patients' bodies wherein various conductive objects, such as artificial joints and other conductive implants, conductive medical instruments and conductive medical apparatus, such as surgical tables, monitors and other equipment, and the like, are likely to remain in the tracking environment during tracking.

Conventional methods for improving the accuracy of magnetic tracking systems include methods that characterize the environment and apply previously stored corrections. These methods apply corrections based on present position and orientation information (see, e.g., U.S. Pat. Nos. 4,622,644 to Hansen and 4,945,305 to Blood, among others). Other methods include signal generating and processing schemes that allow the induced eddy currents, the source of the inaccuracy, to be eliminated. Such systems utilize pulsed-DC or multi-frequency excitations.

Examples of pulsed-DC systems that utilize a plurality of generating and sensing elements are disclosed by Blood in U.S. Pat. No. 4,945,305 and Anderson in U.S. Pat. No. 5,453, 686. The use of pulsed-DC systems reduces the effects of eddy currents by controlling the characteristics of the eddy currents and manipulating the sensed signals so as to minimize their effects, thereby improving accuracy of these systems when conductive materials are present within the tracking environments. A disadvantage of pulsed-DC systems is that they operate only in a time division multiplexed mode. Other drawbacks sometimes include the need for bulky and more complex active sensing devices (compared to sensors used in AC systems). The Blood sensing devices measure field frequencies from DC on up and are thus sensitive to the earth's magnetic field, for which Blood's system must compensate. The broad range of frequency measurement also means that such systems cannot work near medical instruments that operate with large DC magnetic fields, such as magnetic manipulators. The Blood system removes eddy-current-induced inaccuracies by applying a DC excitation signal to a field generator and then curve fitting the decay to extrapolate the final sensed value. The Anderson system eliminates the use of DC sensitive field sensing elements and consequently reduces the complexity of the hardware. His signal processing scheme removes eddy current induced inaccuracies by applying a DC excitation signal to a field generator and integrating the sensed waveform from an AC sensor. This method integrates out the eddy current inaccuracies.

Some conventional DC approaches require an active magnetic sensor that is complex, bulky and has a poor signal-to-noise ratio compared to passive AC magnetic sensors. They are further complicated by the fact that the sensor is sensitive to the earth's magnetic field and processing steps must be included to eliminate the earth's magnetic field. This comes at the expense of the system measurement update rate. Some approaches overcome or reduce some of the disadvantages, but must wait for the eddy currents to die out before determining the value of the field without the deleterious effects of the eddy currents. This too comes at the expense of the system measurement update rate.

Another method for improving accuracy in the presence of conductive materials is disclosed by Rotier in U.S. Pat. No. 4,829,250. The Rotier method is an AC method that includes a plurality of generating and sensing elements and utilizes multi-frequency excitation of the field generator. Eddy current inaccuracies are a function of frequency. This knowledge is utilized by extrapolating to DC a curve fit from a higher frequency to a lower frequency to determine the yaw and pitch angles about a line-of-sight axis, which does not include position.

Another method for improving accuracy in the presence of conductive materials is disclosed by Osadchy et. al. in U.S. Pat. No. 6,147,480. The Osadchy et al. method is an AC method that includes a plurality of generating and sensing elements and utilizes a phase shift detected at the sensing elements and caused by the conductive material. Phase shift differences from a clean baseline (typically zero phase shift) allow the Osadchy et al. system to apply a correction to the measured fields.

Another method of improving accuracy in the presence of conductive materials is disclosed by Ashe in U.S. Pat. No.

6,172,499. The Ashe method is an AC method that includes a plurality of generating and sensing elements and utilizes two excitation frequencies per field generator. The amplitude and phase changes at the two frequencies caused by various distorters at various positions within the tracking volume are stored in a table during manufacture. This table is later accessed during normal operation. Corrections are extracted from the table and applied to the measured fields. The determination of when to use the table is based on the phase shift differences from a clean baseline (typically zero phase shift).

A method further removed from the previously noted techniques for improving accuracy in the presence of conductive materials is disclosed by Elhardt in U.S. Pat. No. 5,347,289. The Elhardt method generates a rotating magnetic field vector of known frequency using a plurality of field generators. Multiple sensors, each with a plurality of sensing elements, are mounted on the object to be tracked. A measurement of the time required for the field vector to pass through a reference point and then through a sensor allows the position of the sensor to be determined. Using multiple sensors mounted in known proximity to one another allows the determination of the orientation of the sensors.

SUMMARY OF THE INVENTION

One implementation of the present invention is a method of determining the location of an object using a tracking system having a distortion threshold. The method includes the steps of: a) collecting magnetic field data from at least one sensor, the magnetic field data containing frequency data for at least one frequency; b) processing the frequency data so as to obtain a real response component and an imaginary response component for the at least one frequency; and c) determining whether to compensate for magnetic field distortion as a function of the real response component, the imaginary response component and the distortion threshold.

Another implementation of the present invention is a computer readable medium containing computer instructions for determining the location of an object using a tracking system having a distortion threshold. The computer instructions include: a) a first set of instruction for collecting magnetic field data from at least one sensor, the magnetic field data containing frequency data for at least one frequency; b) a second set of instructions for processing the frequency data so as to obtain a real response component and an imaginary response component for the at least one frequency; and c) a third set of instructions for determining whether to compensate for magnetic field distortion as a function of the real response component, the imaginary response component and the distortion threshold.

Still another implementation of the present invention is a system for determining the location of an object using a tracking system having a distortion threshold based on a norm of residuals. The system includes: a) a distortion threshold; b) at least one sensor; and c) a processor having an input for receiving magnetic field data from the at least one sensor and operatively configured to: i) collect the magnetic field data, the magnetic field data containing frequency data for at least one frequency; ii) process the frequency data so as to obtain a real response component and an imaginary response component for the at least one frequency; and iii) determine whether to compensate for magnetic field distortion as a function of the real response component, the imaginary response component and the distortion threshold.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein:

FIGS. 3A-3C are schematic diagrams illustrating, respectively, situations S1-S3 of FIGS. 2A and 2B;

DETAILED DESCRIPTION OF THE DRAWINGS

Before discussing details of the invention, some explanation of eddy current errors will initially be given. The induced sensor voltage due to a changing magnetic field is given by:

$$v(t) = -\frac{\partial}{\partial t}\int_S \overline{B} \cdot d\overline{S} \quad \{1\}$$

where v(t) is the induced voltage and $\overline{B}$ is the magnetic flux density in the direction of $\overline{S}$, the surface that encloses $\overline{B}$ (in all cases, the sensor surface area). $\overline{B}$ is proportional to the current flowing in the field generator element. Electromagnetic tracking systems with multiple B-field generating elements can time or frequency multiplex the B-field generators to distinguish the induced sensor signals generated by each generator. Time multiplexing is the only method that can presently be used with pulsed-DC electromagnetic tracking systems.

The present inventor has found that the frequency response of a sensor due to the field generator B-field and the B-field due to eddy currents can be represented in terms of lead, lag or lead-lag networks. This can be written succinctly in terms of a Laplace transform as:

$$H_{sensor}(s) = k \sum_j \frac{s+z_j}{s+p_j} \quad \{2\}$$

where $H_{sensor}(s)$ is the transfer function relating the output of the sensor to the field excitation; k is a gain constant; and $z_j$ and $p_j$ are, respectively, the zeros and poles of the network and are related to the characteristics of the conductive distorter and its position and orientation with respect to the sensor and field generator. This has been born out by experimental measurement and simulation.

Figure 1A:
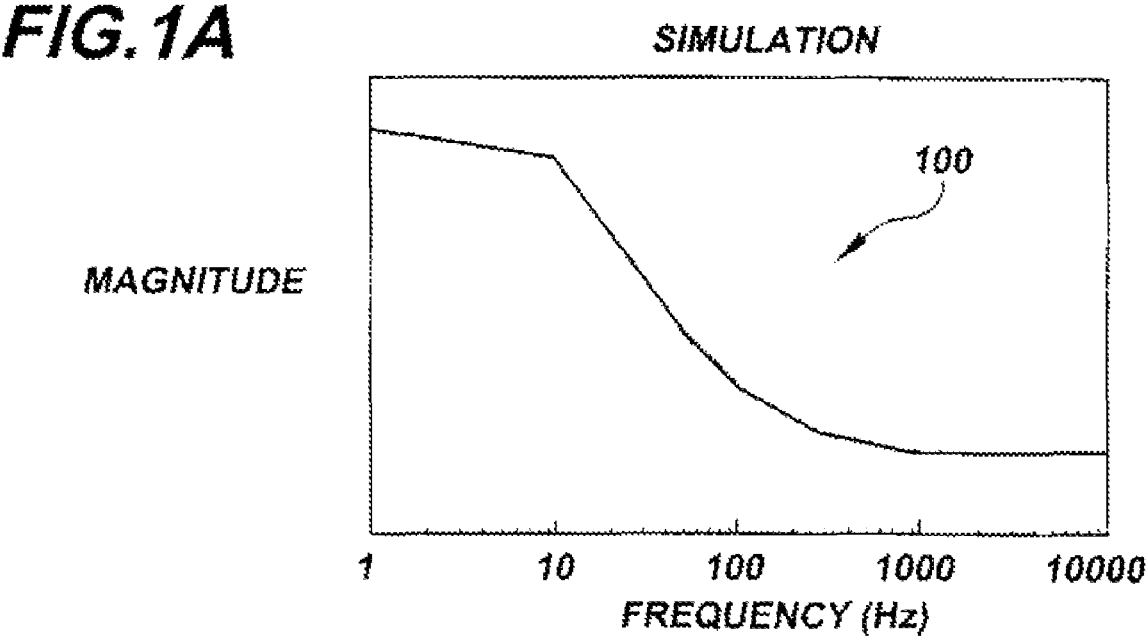
FIGS. 1A and 1B are, respectively, graphs of the magnitude and phase of eddy current effects of a simulated conductive distorter on a sensor.
Figure 1B:
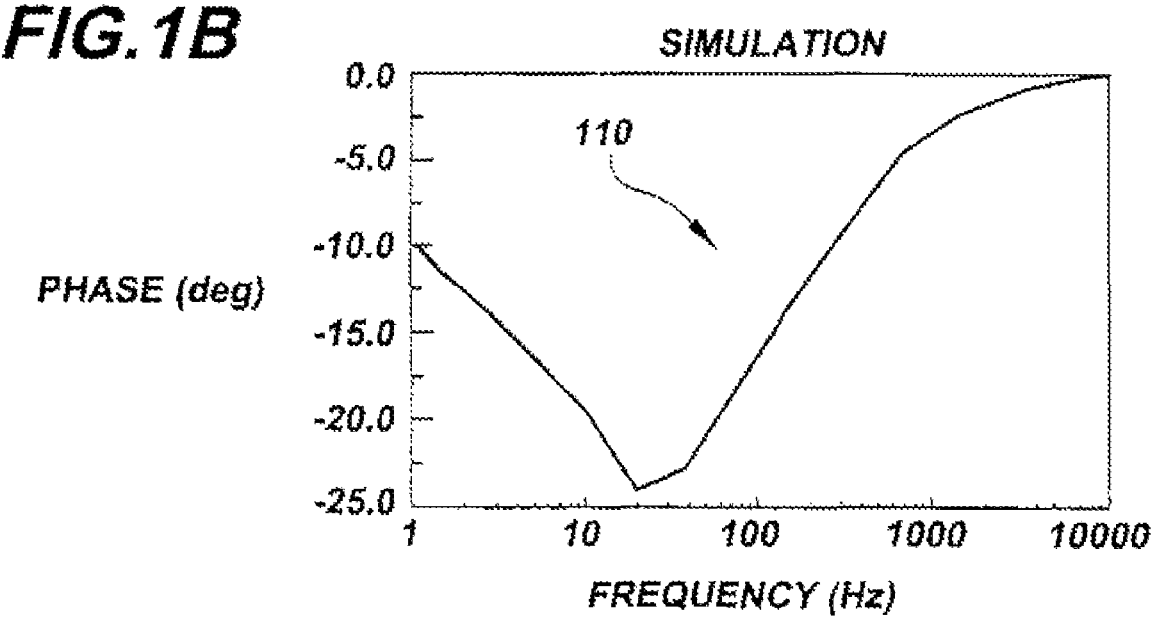
Figure 2A:
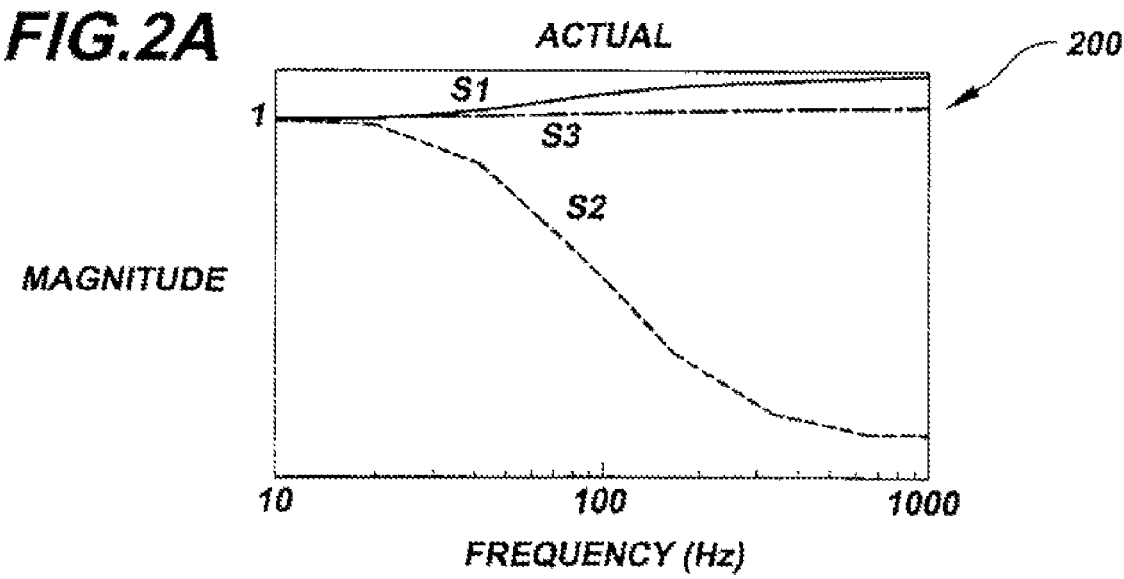
FIGS. 2A and 2B are, respectively, graphs of the magnitude and phase of eddy current effects of an actual conductive distorter on a sensor placed at three different positions (situations S1-S3)
Figure 2B:
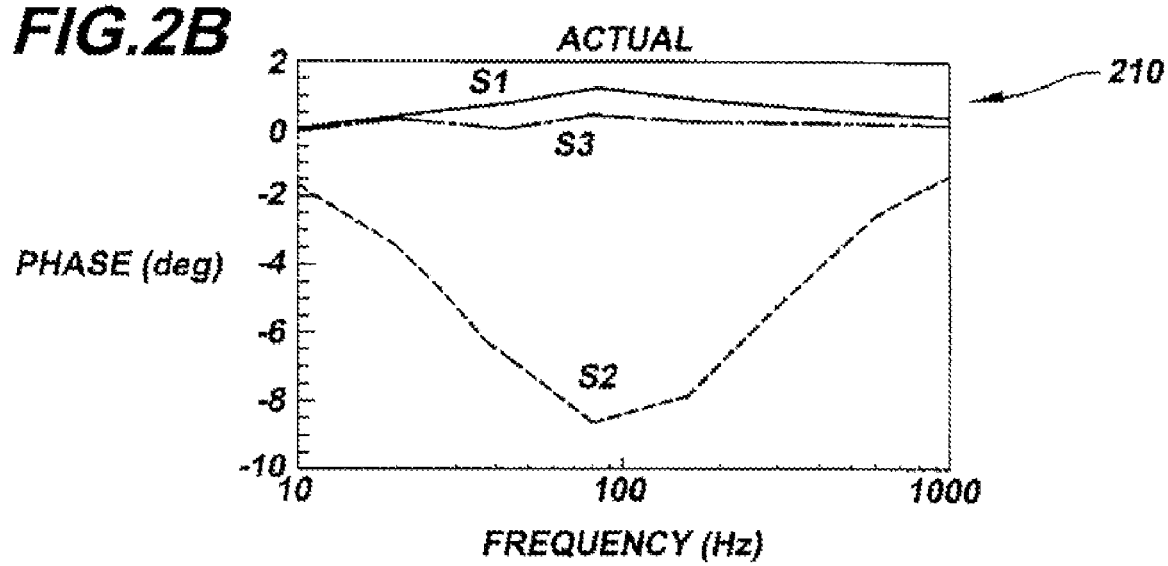

FIGS. 1A and 1B illustrate simulated frequency response data from a sensor of an AC-type tracking system, such as AC tracking system 600 of FIG. 6, described in detail below. The condition was a conductive distorter located close behind the sensor, both of which were in front of, and away from, a field generator (this condition is similar to situation S2 illustrated in FIG. 3B). FIG. 1A is a plot 100 of the simulated magnitude response and FIG. 1B is a plot 110 of the simulated phase response. FIGS. 2A and 2B show, respectively, a plot 200 of measured magnitude and a plot 210 of phase data from three different physical situations S1, S2, S3 illustrated, respectively, in FIGS. 3A-3C. Situations S1, S2, S3 show a B-field source 310 and a magnetic sensor 320 in different positions relative to a conductive distorter 330. Note the similarity between the data in plots 100, 110 of FIGS. 1A and 1B and the data for Situation S2 in plots 200, 210 FIGS. 2A and 2B.

Eddy current reduction is carried out by collecting sufficient data to determine the parameters k, $p_j$ and $z_j$ in Equation {2}, above. The undistorted field value is taken as the resulting value of:

$$k \prod_j \frac{p_j}{z_j} \quad \{3\}$$

since this is the value of the network at zero Hertz, i.e., where conductive distortion no longer exists. The data collected by the sensor includes the response of the sensor to a multiple frequency excitation. The data is then analyzed for magnitude and phase changes or, equivalently, for real and imaginary component changes. The minimum number of frequencies is two, which provides two magnitudes and two phases (providing four equations) for determining three unknown parameters (for j=1). The determination of additional terms of Equation {2} requires additional excitation frequencies.

The magnitude (H(w)) and phase (Θ(w)) of Equation {2} when j=1 are:

$$H(w) = k \frac{\sqrt{w^2 + z^2}}{\sqrt{w^2 + p^2}} \quad \{4a\}$$

$$\Theta(w) = \tan^{-1}(w/z) - \tan^{-1}(w/p) \quad \{4b\}$$

where w is the frequency in radians. The measurement of the magnitude and phase (or real and imaginary components, respectively) can be accomplished a number of ways well known in the art, such as coherent detection, discrete and fast Fourier transforms (DFT and FFT, respectively), sliding FFTs, chirp Z transforms, Hartley and wavelet transforms, and analog and/or digital filters, among others. The most commonly used method is coherent detection.

Typically, a sinusoidal (sin(wt)) excitation of the field generator may be used. Such an excitation is sensed as:

$$v = f(\text{position,orientation})(-w \cos(wt)) \quad \{5\}$$

where v is the sensed voltage induced across the sensor, f is a gain related to the position and orientation of the sensor with respect to the transmitter and the −w cos(wt) term is due to Equation {1}. The amplitude of the sensed signal increases linearly as a function of w. Therefore, the sensed signals must be normalized (i.e., the frequency effect removed) before using the signal to define a valid frequency response. The sensed signal may be multiplied individually by cos(wt) and sin(wt) (also known as demodulation) and either integrated over an integer number of cycles or filtered, respectively, to obtain the real (R) (or in-phase) and imaginary (I) (or out-of-phase) components of the signal. The magnitude and phase can then be determined by:

$$H(w) = \sqrt{(R^2 + I^2)} \quad \{6a\}$$

$$\Theta(w) = \tan^{-1}(I/R) \quad \{6b\}$$

Once H(w) and Θ(w) are known at two different frequencies w, they can be inserted into Equations {4a} and {4b}, which can then be solved for the parameters k, p and z. Sensors that are not based on the rate of change of the field (as in Equation {1}) can also use this method. Such sensors do not require the frequency normalization noted above.

There are many methods for solving for the parameters k, p and z. Since there are more equations than unknown parameters, a least-squares approach can be used. The least-squares approach is generally: given m functions $f_1, f_2, \ldots, f_m$ of the n variables $x_1, x_2, \ldots, x_n$, with m≧n, find values for $x_1, x_2, \ldots, x_n$ that solve the nonlinear least squares problem, $$\min\left\{\sum_{i=1}^m f_i(x)^2 : x \in R^n\right\} \quad \{7\}$$

Many well-known methods exist to help solve such problems. The predominant methods require the evaluation of the Jacobian (i.e., a matrix of partial derivatives of the equations with respect to the unknowns), either explicitly or by finite differences and sometimes requiring the evaluation of the Hessian (i.e., a matrix of second partial derivatives of the equations with respect to the unknowns). These methods are often referred to as Newton methods, gradient methods or steepest-descent methods, or variations on this theme. Numerical Recipes in Fortran, $2^{nd}$ Edition, by Press et al., Cambridge University Press 1992, and User Guide for MINPACK-1, Argonne National Laboratory, 1980, provide details on these methods.

The foregoing methods are iterative and require additional program space and computing power. Therefore, a simpler method to solve for the parameters is desirable. For the case of j=1, parameters k, p and z can be solved explicitly in terms of the real and imaginary components as follows:

$$p = \sqrt{\frac{-(-w_1 I_2 + I_1 w_2) w_1 w_2 (-w_2 I_2 + I_1 w_1)}{(-w_1 I_2 + I_1 w_2)}} \quad \{8a\}$$

$$z = \frac{-w_1(I_1^2 w_2 w_1 - w_1^2 I_2 I_1 - \sqrt{-(-w_1 I_2 + I_1 w_2) w_1 w_2 (-w_2 I_2 + I_1 w_1)} R_1}{\left(\sqrt{-(-w_1 I_2 + I_1 w_2) w_1 w_2 (-w_2 I_2 + I_1 w_1)} I_1 - w_1^2 R_1 I_2 + w_1 R_1 I_1 w_2\right)} \quad \{8b\}$$

$$k = \frac{\sqrt{-(-w_1 I_2 + I_1 w_2) w_1 w_2 (-w_2 I_2 + I_1 w_1)} I_1 - w_1^2 R_1 I_2 + w_1 R_1 I_1 w_2}{(-w_1 I_2 + I_1 w_2) w_1} \quad \{8c\}$$

where $w_1$ and $w_2$ represent two excitation frequencies, respectively; $R_1$ represents the real component at $w_1$; and $I_1$ and $I_2$ represent the imaginary components at $w_1$ and $w_2$, respectively. Note that the second real component ($R_2$) is not used. Other sets of equations can be derived using other combinations of components, as well as averaging the resulting parameters determined from various combinations, as would be known in the art. Additional and more complicated closed-form solutions result when $j \geq 2$.

The excitation frequencies must fall within a narrow band to be useful. For greatest sensitivity, the frequencies should range between 10 and 1,000 Hz, with pairs of frequencies being spaced at least 100 Hz apart. This frequency range is where the effects from the conductive distorter are most discernible. Others, such as Ashe in U.S. Pat. No. 6,172,499, have realized this. Two or more frequency excitations can also be accomplished by using harmonically rich excitation waveforms, as disclosed by the present inventor in U.S. Pat. No. 6,427,079, which is incorporated by reference herein.

Further enhancement of the present invention can be accomplished by focusing on the manner of multiplexing the transmitter excitations. Electromagnetic tracking systems use either time division multiplexing, frequency division multiplexing or both to distinguish between fields generated by different transmitters. When time multiplexing is used there are always eddy current transients generated. This can be seen by examining the impulse response (Laplace transform) of Equation {2} (for j=1)

$$h_{sensor}(t) = k(\delta(t) + (z-p)e^{-pt}) \quad \{9\}$$

where $h_{sensor}(t)$ is the impulse response; t is time, $\delta(t)$ is the unit impulse, k is a gain constant, z and p are, respectively, the zero and pole of the network and are related to the characteristics of the conductive distorter and its position and orientation with respect to the sensor(s) and field generator(s) and e is the exponential function. Convolving Equation {9} with the time domain representation of the generator excitation yields the sensed sensor signal affected by a conductive distorter. Another way to interpret this is to note that convolving a waveform with the unit impulse yields the waveform, convolving a waveform with the function $(z-p)e^{-pt}$ yields an amplitude-modified, phase-shifted waveform plus exponentially decaying transient terms. It is these same transients that pulsed-DC electromagnetic tracking systems combat by watching and evaluating their decay (see, e.g., U.S. Pat. Nos. 4,849,692 and 4,945,305 to Blood).

These transients appear as other frequency and phase components in the frequency response and corrupt the measured real (R) and imaginary (I) components of the sensed signal. There are two preferred, but not exclusive, methods for reducing the effects of transients. One method, used when time division multiplexing the transmitter excitation, waits a period of time after the transmitter excitation has started before measuring the real (R) and imaginary (I) components. This allows some portion of the transient to die away. When using demodulation with integration, a delay of an integer number of cycles is preferred. When demodulating and filtering, a delay sufficient to allow most of the transient to settle out of the filter is preferred.

Another method that can be used with time division multiplexing is to fit the time response. A suitable model can be derived by taking the inverse Laplace transform of the transfer function (Equation {2}) times the Laplace transform of the excitation waveform. A method similar to this is disclosed by the present inventor in U.S. Pat. No. 6,427,079, which has been incorporated herein by reference above. However, it has been found that this method is much more sensitive to measurement errors and generally yields poorer results than frequency domain methods.

The other preferred method utilizes continuous transmitter excitation in a frequency division multiplexed manner. Continuous excitation eliminates the startup transient inherent in time-division multiplexing. While transients are generated as a conductive distorter is moved, they are of far less consequence when compared to excitation transients. The excitations can be sets of two sinusoids or, as disclosed by the present inventor in U.S. Pat. No. 6,427,079, can be harmonically rich waveforms running continuously. Examples of suitable harmonically rich waveforms include square waves and triangular waves. It is generally only required that spectra from the various sensed waveforms do not overlap at the frequencies of interest.

Figure 4A:
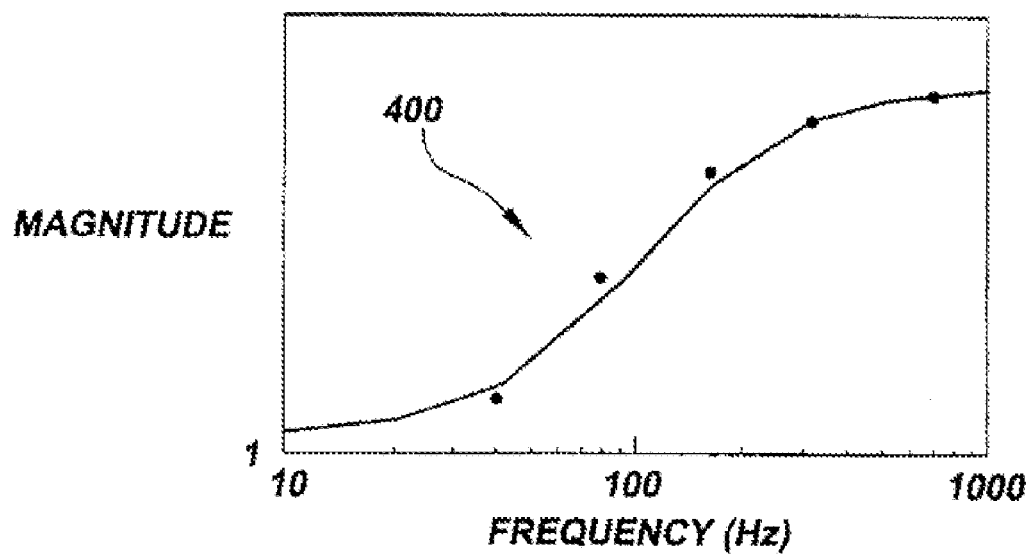
FIGS. 4A and 4B are, respectively, graphs of magnitude and phase of data presented in FIGS. 2A and 2B illustrating a method of the present invention for correcting inaccuracies caused by eddy current effects.
Figure 4B:
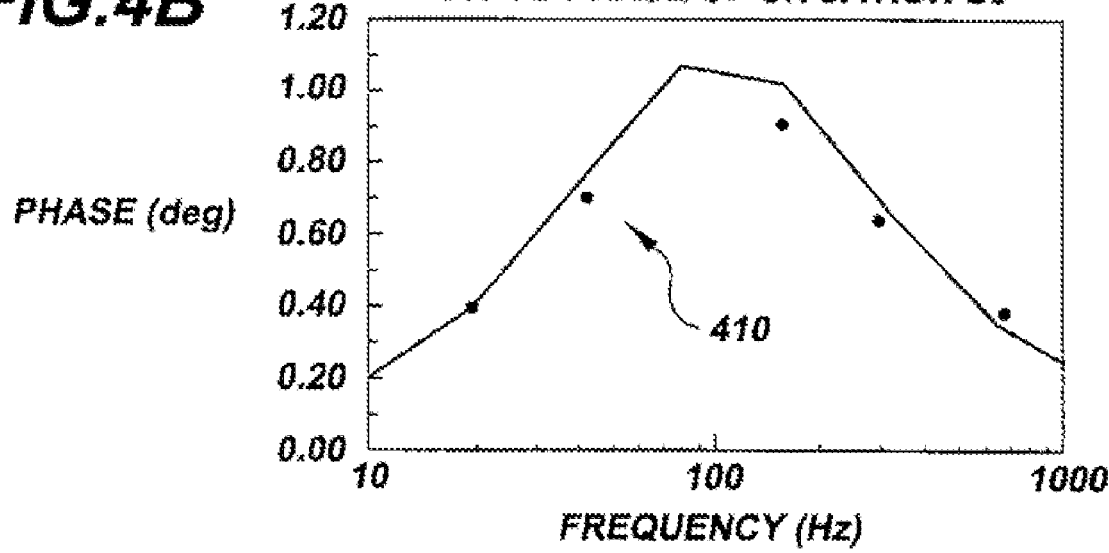
Figure 5:
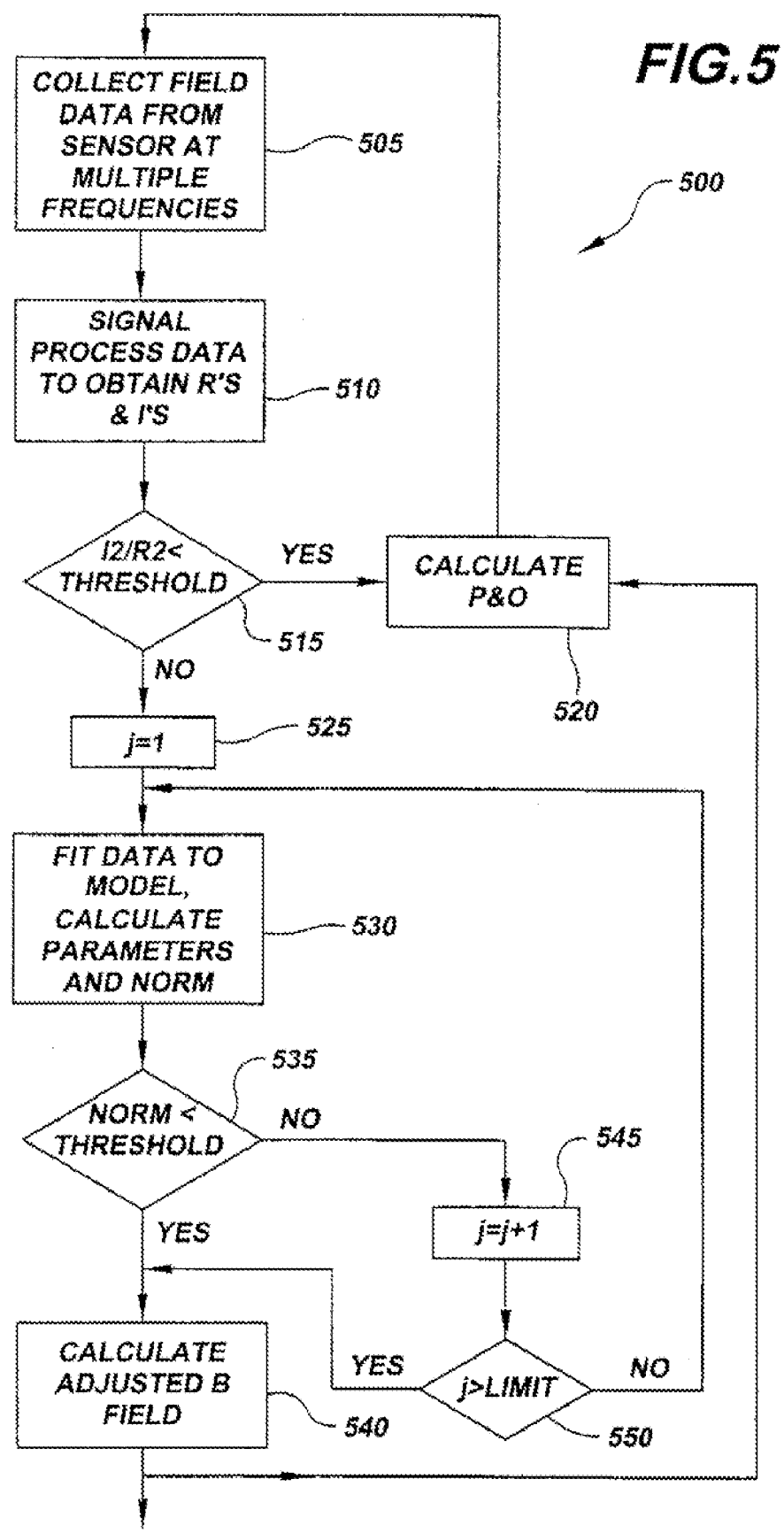
FIG. 5 is a flow chart of the method of FIGS. 4A and 4B.

It has been found that for most practical purposes modeling the frequency response with one network (j=1) provides sufficient accuracy when a single, dominant distorter, such as a medical instrument in a medical tracking application, is present. Of course, j may be greater than one depending on the situation, e.g., the number of distorters. FIG. 5 illustrates an adaptive distortion compensation method 500 of the present invention for setting j and number of excitation frequencies per transmitter. FIGS. 4A and 4B show, respectively, a magnitude plot 400 and a phase plot 410 of data presented in FIGS. 2A and 2B relative to situation S3 that illustrate results of the application of distortion compensation method 500. Method 500 is described in more detail below.

How accurately the parameters k, $z_j$ and $p_j$ fit Equation {2} may be measured by the norm of the residuals. The norm of the residuals is defined as the square root of the sum of the squares of the modeling function minus the measured value, when evaluated at the determined parameters. This is illustrated in Equation {10}.

$$norm = \sqrt{\left(\frac{k\sqrt{w^2+z^2}}{\sqrt{w^2+p^2}} - \sqrt{(R^2+I^2)}\right)^2 + \left(\tan^{-1}\left(\frac{w}{z}\right) - \tan^{-1}\left(\frac{w}{p}\right) - \tan^{-1}\left(\frac{I}{R}\right)\right)^2} \quad \{10\}$$

Here, Equations {4} and {6} are used to represent the model and the measured values, respectively. In practice, a system will produce a small but finite norm in an environment that contains no magnetic distorters (i.e., highly-conductive materials). The value of this norm can be determined experimentally within a distorter-free environment and represents the THRESHOLD noted in steps 535 and 515 of method 500.

Referring in detail to FIG. 5, in step 505 magnetic field data from the field generators is sampled at the sensor(s). In step 510, the data is processed to obtain the real (R) and imaginary (I) components of the sensed signal. This processing may be performed using any method for determining in-and-out-of-phase signal components known in the art, such as the techniques noted above. In step 515, the ratio of the imaginary to the real response for the second (higher) frequency I2/R2 may be evaluated. The second frequency is chosen here because it is more sensitive to conductive distorters. A small value of I2/R2, i.e., a value less than THRESHOLD, indicates that little or no distortion is present and that the real component may be used in step 520 to calculate position and orientation (P&O). Otherwise, at step 525 a model with one p and one z, i.e., j=1 may be assumed. At step 530, the parameters k, p and z may calculated from Equation {8} and the norm calculated from Equation {10}. If, at step 535, the norm is less than THRESHOLD the adjusted B-field may be calculated at step 540 using Equation {3} and supplied to the P&O algorithm at step 520. The cycle is then started over at step 505.

If at step 535 the norm is greater than or equal to THRESHOLD, the number of model parameters is increased at step 545 by incrementing j by one to increase the accuracy of the model. After j is incremented at step 545, j is evaluated at step 550 to determine whether it is greater than a predefined limit LIMIT that places an upper constraint on the number of parameters (p's and z's) that must be determined. While it is believed that j=4 would cover almost all tracking applications, there is generally no reason not to allow j to be greater other than practical reasons, such as computing power. Upper LIMIT on j would depend mainly on the processing time for computing the model. If j exceeds value of LIMIT, the adjusted B field may be calculated in step 540 from Equation {3} and supplied to the P&O algorithm at step 520. Otherwise, the next set of frequency data is incorporated to fit the model in step 530 and the process repeated until either the norm is less than THRESHOLD or the LIMIT relative to j is reached. It should be appreciated by those skilled in the art that the model order j does not have to be determined to completion at the end of each cycle. Rather, j could be adjusted up or down by one each cycle in an iterative manner.

Figure 6:
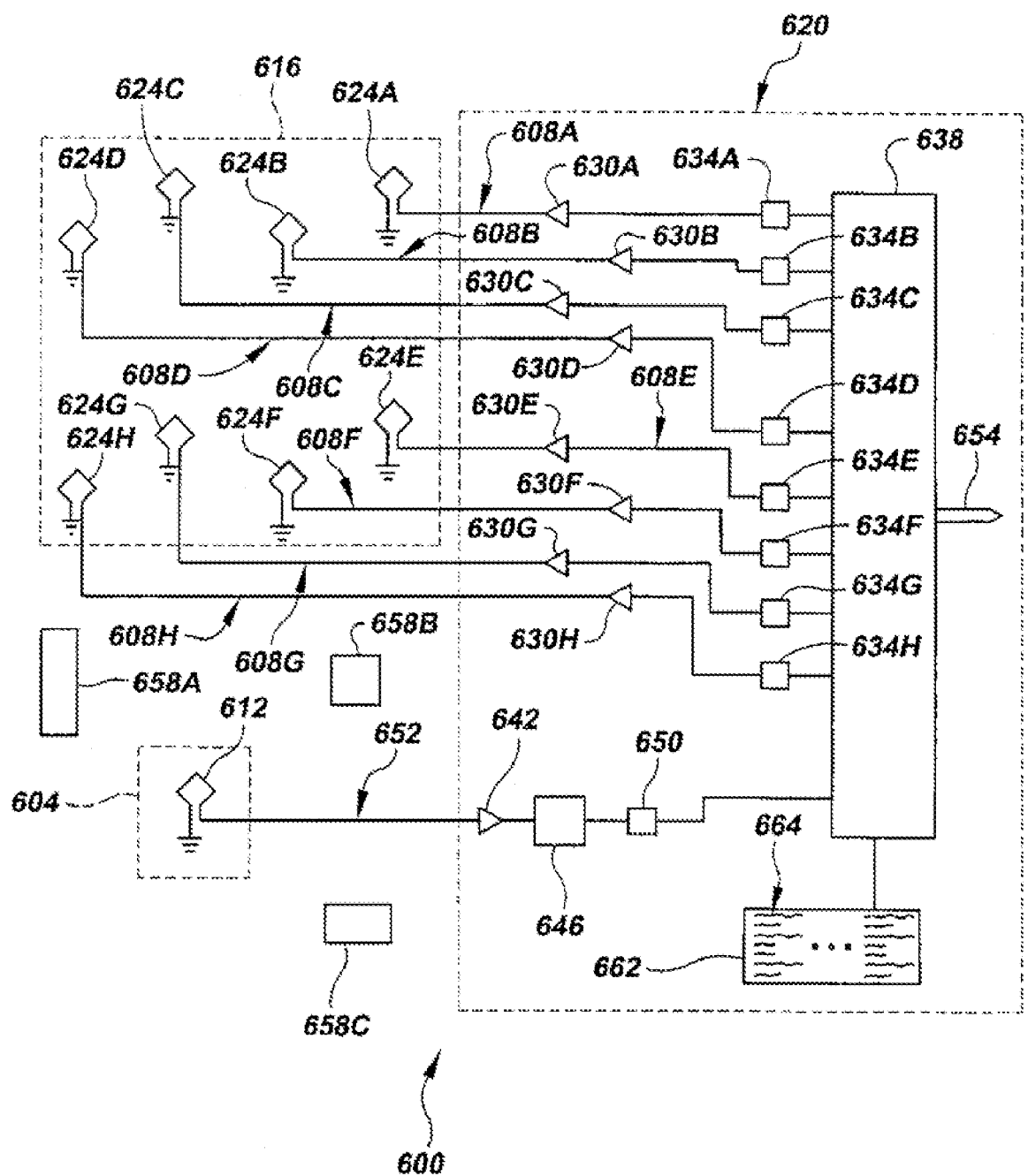
FIG. 6 is a simplified schematic diagram illustrating components of a position and orientation determination system of the present invention.

FIG. 6 illustrates a system 600 of the present invention that may be used for determining the position and orientation of a remote object 604 relative to a coordinate reference frame (not shown). System 600 may include one or more generators of electromagnetic fields, e.g., generators 608A-H, a remote sensor 612, a transmitter tablet 616 and a tracking processor 620 for processing transmitter and sensor signals. A mode of operation of system 600, including appropriate techniques for determining position and orientation of sensor 612 relative to the reference coordinate frame of transmitter tablet 616, is disclosed by the present inventor in U.S. Pat. No. 6,427,079, incorporated herein by reference above. However, other operating modes could be used in conjunction with the eddy current compensation method disclosed herein. For example, Jones (U.S. Pat. No. 4,737,794), Martinelli (U.S. Pat. No. 5,592,939), Blood (U.S. Pat. No. 5,600,330), Dumoulin (U.S. Pat. No. 5,377,678), Rorden (U.S. Pat. No. 4,710,708), Bladen (International Patent Publication WO 94/04938) and Ben Haim (International Patent Publication WO 96/05768), among others, each disclose modes of operation that could be improved with the eddy current compensation methods disclosed herein and discussed in more detail below. Each of the references is incorporated herein by reference.

In order to separate the contributions from the various field generators 608A-H as measured at the sensor frequency division multiplexing may be performed. This means that the excitations of field generators 608A-H must be at different frequencies. By judicial choice of excitation frequencies, the spectrums of the sensed waveforms can be made distinct. Some methods for accomplishing this are disclosed by the present inventor in U.S. Pat. No. 6,427,079.

Transmitter tablet 616 includes a plurality of field generating elements, such as transmitter antennas 624A-H. Antennas 624A-H need only be spatially and rotationally distinct such that the field generated by each antenna be distinguishable at sensor 612 and that there is a unique set of field values at all positions within the measurement volume. Antennas 624A-H are typically eight magnetic loop windings of circular or rectangular geometry, but other geometries are possible. Antennas 624A-H are supplied with AC triangular waveforms of different frequencies by corresponding current drivers 630A-H. The signals are frequency division multiplexed so that the fields generated by each antenna 624A-H are distinguishable from the fields generated by the other antennas. This frequency division multiplexing may be accomplished by a set of digital-to-analog converters (DACs) 634A-H, each corresponding to a respective one of transmitter antennas 624A-H. DACs 634A-H may be driven by a digital signal processor (DSP) 638 within tracking processor 620 to generate the analog signals that are supplied as inputs to current drivers 630A-H. It should be understood that, in the illustrated embodiment, eight current drivers 630A-H, or power amplifying circuits, are provided, each being connected to a corresponding one of eight field generating antennas 624A-H with eight DACs 634A-H applying actuation signals simultaneously to each of the antennas through the eight individual driving circuits.

Sensor 612 is preferably, but not necessarily, a passive loop antenna that responds to the rate of change of magnetic field dB/dt. The output of sensor 612 may be supplied to a differential preamplifier 642. The output of preamplifier 642 may be supplied to an anti-aliasing filter 646 having a frequency response chosen to prevent aliasing of the sampled data while allowing suitable sensed harmonic content of the frequency division multiplexed signals to pass unaffected to an analog-to-digital converter (ADC) 650. Sensor 612, preamplifier 642, anti-aliasing filter 646 and ADC 650 may be considered to form a sensor circuit 652. ADC 650 converts the output of amplifier 642 to a discrete time digital representation for processing by DSP 638. ADC 650 converts analog data at a rate suitable for FFT processing and chosen such that the sampled signals spectra falls exactly within the FFTs frequency bins and contains no spectral leakage. In the preferred DSP 638, the DSP adaptively picks which of the excitation waveforms harmonics to use.

DSP 638 provides the necessary timing signals for driving DACs 634A-H and reading the data from ADC 650. DSP 638 also calculates the position and orientation of sensor 612 in a reference coordinate frame defined by transmitter tablet 616 and may supply the results to other systems via interface 654. In the illustrated embodiment, the frequency multiplexed AC excitation frequencies are used. However, it should be apparent to those skilled in the art that time multiplexed, and time and frequency multiplexed waveforms could also be used with this technique.

Referring to FIG. 6, and also to FIG. 5, system 600 may utilize method 500 of FIG. 5 to remove, or at least lessen, the effects of eddy currents within conductive distorters, e.g., conductive distorters 658A-C shown in FIG. 6. In this case, data may be collected by DSP 638 at step 505 via sensor circuit 652. In the preferred embodiment the number of data points is dependent on the rate of data conversion of ADC 650 as well as its suitability for signal processing. The rate is chosen such that the sampled signals spectra contains no spectral leakage. DSP 638 collects all the data points from ADC 650, processes the data at step 510 and utilizes the in-and-out-of-phase frequency components to perform the modeling of the data in step 530. DSP 638 may also perform the steps of determining the number of networks needed to achieve a desirable result, i.e., steps 515, 525, 535, 545 and 550, as well as step 540 of calculating the adjusted B field and step 520 of calculating the position and orientation of sensor 612 using the lead-lag network methods discussed above. System 600 may further include one or more memories 662, e.g., RAM, ROM, magnetic, optical, etc., that contain the computer instructions 664 necessary for DSP 638 to perform its various functions, such as the functions necessary to perform all or part of method 500 and all or part of the lead-lag network modeling described above.

It should be appreciated by those skilled in the art that system 600 could be reversed, i.e., a driver excitation could be output to a single transmitter antenna and multiple sensor antennas could simultaneously measure the field. Also, since all real measurement systems have a finite bandwidth, the system will have its own intrinsic low-pass filter response that can be characterized in terms of the $z_j$ and $p_j$ parameters. These could be measured at the time of manufacture and stored for use during normal system operation.

Multiple sensors 612 can be used for forming three-dimensional echocardiograms by tracking a handheld ultrasound scanner head. In still another application, multiple sensors 612 can be associated with a particular body part for the purpose of conducting biomechanical studies. Still another application involves the monitoring of the body movements of an invalid for the purpose of creating a nonverbal communication system or providing a technique for remotely controlling various devices with nonverbal communicative body motion. Another application is the tracking of head movements for use in virtual reality headsets. Still another application is a three-dimensional (3-D) mouse for navigating in multidimensional databases or as a tool for use with VRML, a 3-D file format popular on the Internet.

Although specific constructions have been presented herein, it is to be understood that these are for illustrative purposes only. Various modifications and adaptations will be apparent to those of skill in the art. In view of this, it will be appreciated that the scope of the present invention should be determined by reverence to the claims appended hereto, rather than the particular exemplary embodiment described above.

What is claimed is:

1. A computer readable storage medium containing computer-executable instructions for determining the location of an object using a tracking system having a distortion threshold, said computer-executable instructions comprising:

a first set of computer-executable instruction for collecting magnetic field data from at least one sensor, said magnetic field data containing frequency data for at least one frequency;

a second set of computer-executable instructions for processing said frequency data so as to obtain a real response component and an imaginary response component for said at least one frequency; and a third set of computer-executable instructions for determining whether to compensate for magnetic field distortion as a function of said real response component, said imaginary response component and the distortion threshold;

wherein the distortion threshold is a function of a norm of residuals and said third set of computer-executable instructions includes instructions for comparing to the distortion threshold a ratio of said imaginary component to said real component.

2. A computer readable storage medium according to claim 1, further comprising a fourth set of computer-executable instructions for compensating, when said ratio is no less than said distortion threshold, for magnetic field distortion based on a representation of said frequency data comprising at least one lead-lag network having a plurality of parameters.

3. A computer readable storage medium according to claim 2, further comprising:

a) a fifth set of computer-executable instructions for calculating, when said ratio is no less than said distortion threshold, said plurality of parameters and a norm that is a function of said parameter; and b) a sixth set of computer-executable instructions for comparing said norm to said distortion threshold.

4. A computer readable storage medium according to claim 3, further comprising a seventh set of computer-executable instructions for calculating an adjusted B-field when said norm is less than said distortion threshold.

5. A computer readable storage medium according to claim 3, further comprising an eighth set of computer-executable instructions for compensating for magnetic field distortion based on a representation of said frequency data comprising at least two lead-lag networks when said norm is not less than said distortion threshold.

* * * * *